United States Patent
Michalsky et al.

(10) Patent No.: US 10,315,967 B2
(45) Date of Patent: Jun. 11, 2019

(54) THERMOCHEMICAL AMMONIA AND HYDROCARBONS

(71) Applicant: KANSAS STATE UNIVERSITY RESEARCH FOUNDATION, Manhattan, KS (US)

(72) Inventors: Ronald Michalsky, Zurich (CH); Peter Pfromm, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 284 days.

(21) Appl. No.: 14/647,209

(22) PCT Filed: Nov. 25, 2013

(86) PCT No.: PCT/US2013/071704
§ 371 (c)(1),
(2) Date: May 26, 2015

(87) PCT Pub. No.: WO2014/082038
PCT Pub. Date: May 30, 2014

(65) Prior Publication Data
US 2015/0315032 A1    Nov. 5, 2015

Related U.S. Application Data

(60) Provisional application No. 61/729,850, filed on Nov. 26, 2012.

(51) Int. Cl.
*C07C 1/32* (2006.01)
*C07C 1/10* (2006.01)
(Continued)

(52) U.S. Cl.
CPC ............... *C07C 1/32* (2013.01); *B01J 19/127* (2013.01); *B01J 38/04* (2013.01); *C01B 3/025* (2013.01);
(Continued)

(58) Field of Classification Search
CPC .. C07C 1/00; C07C 1/06; C07C 1/063; C07C 1/066; C07C 1/10; C07C 1/12;
(Continued)

(56) References Cited

U.S. PATENT DOCUMENTS 2,478,899 A * 8/1949 D Ouville ............... B01J 23/94
                                                        502/53
4,142,993 A   3/1979 Elofson et al.
(Continued)

FOREIGN PATENT DOCUMENTS

JP    2005075761 A  *  3/2005
WO    00/44965         8/2000
(Continued)

OTHER PUBLICATIONS

English machine translation of JP 2005-075761 A (Year: 2005).*
(Continued)

*Primary Examiner* — Harold Y Pyon
*Assistant Examiner* — Matthew R Diaz
(74) *Attorney, Agent, or Firm* — Hovey Williams LLP (57) ABSTRACT

Reactant materials for use in the synthesis of compounds comprising a non-metal and hydrogen, and methods of making and using the same are provided. The reactant materials generally comprise first and second non-metals, metals, a cation, and a transition metal, and can be formed and used in reactions occurring at relatively low-pressure conditions using heat energy that can be supplied via solar radiation. In particular, the reactant materials can be used in the synthesis of ammonia and various hydrocarbon compounds using air, water, and sunlight.

17 Claims, 5 Drawing Sheets

(51) Int. Cl.
*C07C 29/151* (2006.01)
*B01J 38/04* (2006.01)
*B01J 19/12* (2006.01)
*C01B 3/06* (2006.01)
*C01B 21/06* (2006.01)
*C01B 3/02* (2006.01)
*C01C 1/02* (2006.01)
*C01B 21/16* (2006.01)

(52) U.S. Cl.
CPC .......... *C01B 3/06* (2013.01); *C01B 21/0602* (2013.01); *C01B 21/0637* (2013.01); *C07C 1/10* (2013.01); *C07C 1/321* (2013.01); *C07C 1/325* (2013.01); *C07C 1/328* (2013.01); *C07C 29/1518* (2013.01); *C01B 21/16* (2013.01); *C01C 1/026* (2013.01); *C01P 2002/54* (2013.01); *Y02E 60/36* (2013.01); *Y02P 20/582* (2015.11)

(58) Field of Classification Search
CPC ....... C07C 1/043; C07C 1/0435; C07C 1/044; C07C 1/0445; C07C 1/045; C07C 1/32; C07C 1/321; C07C 1/323; C07C 1/325; C07C 1/326; C07C 1/327; C07C 1/328; C07C 39/1518; C07C 39/153; C07C 39/154; C07C 39/156; C07C 39/157; C07C 39/158; C07C 29/1518; C07C 29/153; C07C 29/154; C07C 29/156; C07C 29/157; C07C 29/158; C01B 3/06; C01B 3/061; C01B 3/063; C01B 3/065; C01B 3/08; C01B 3/16; C01B 3/17; C01B 3/20; B01J 19/12; B01J 19/122; B01J 19/123; B01J 19/124; B01J 19/125; B01J 19/126; B01J 19/127; B01J 19/128; B01J 19/129; B01J 38/04; B01J 2523/00; B01J 38/06; B01J 38/08; B01J 38/10
See application file for complete search history.

(56) References Cited

U.S. PATENT DOCUMENTS

| 4,595,703 A | * | 6/1986 | Payne | B01J 23/75 |
| | | | | 208/950 |
| 4,883,559 A | | 11/1989 | Bamberger | |
| 6,077,371 A | | 6/2000 | Lundstrom et al. | |
| 2011/0201698 A1 | * | 8/2011 | McAlister | B01J 19/127 |
| | | | | 518/700 |
| 2012/0315215 A1 | * | 12/2012 | Barenbaum | C01B 3/06 |
| | | | | 423/579 |

FOREIGN PATENT DOCUMENTS

WO   WO-2011060556 A1 *  5/2011  ........... B01D 53/047
WO   WO 2012119958 A1 *  9/2012  ......... C07C 29/1518

OTHER PUBLICATIONS

Absorption. Hawley's Condensed Chemical Dictionary. (Year: 2007).*
Yamauchi et al. "Absorption and Release of Carbon Dioxide with Various Metal Oxides and Hydroxides" Materials Transactions, vol. 48, No. 10, 2739-2742. (Year: 2007).*
Michalsky, Ronald, "Solar thermochemical production of ammonia from water, air and sunlight: Thermodynamic and economic analyses," Energy, 2012, pp. 251-260, vol. 42, Elsevier Ltd.
Galvez, M. E. "Ammonia Production via a Two-Step Al2O3/AlN Thermochemical Cycle. 1. Thermodynamic, Environmental, and Economic Analyses," Ind. Eng. Chem. Res. Feb. 21, 2007, pp. 2042-2046, vol. 46, American Chemical Society.
International Search Report and Written Opinion dated Mar. 14, 2014, in PCT/US2013/071704, filed Nov. 25, 2013.

* cited by examiner

THERMOCHEMICAL AMMONIA AND HYDROCARBONS

RELATED APPLICATIONS

This is a national stage application under 35 U.S.C. § 371 of International Application No PCT/US2013/071704, filed Nov. 25, 2013, which claims benefit of U.S. Provisional Patent Application No. 61/729,850, filed Nov. 26, 2012, both of which are hereby incorporated by reference in their entireties

STATEMENT REGARDING FEDERALLY SPONSORED RESEARCH

This invention was made with U.S. Government support under grant number IGERT-0903701 awarded by the National Science Foundation. The government has certain rights in the invention.

BACKGROUND OF THE INVENTION

Field of the Invention

The present invention is directed toward materials and methods for producing compounds comprising a first non-metal and hydrogen, and in particular, ammonia and various hydrocarbon compounds. Thermodynamically stable reactant materials are provided that comprise a transition metal, a metal cation, and first and second non-metals. Upon reaction with a source of hydrogen, namely water, the first non-metal is liberated from the reactant and hydrogenated to form the desired product compound. Synthesis and use of the reactant materials may be accomplished using solar energy thereby achieving synthesis of ammonia and hydrocarbon compounds through the use of air, water, and sunlight.

Description of the Prior Art

Ammonia is of utmost importance as a fertilizer for adequate food production. Without manmade ammonia there would be inadequate nutrition for a significant portion of the world's population. Rising food demand will further increase the importance of ammonia worldwide. Industry is investing in expanded fertilizer production capacity (for example forecasted $3.8 billion spent by CF Industries, Illinois, through 2016). Ammonia is one of the most produced chemicals in the world and its production consumes about 2% of the world's annual energy budget, mainly in the form of natural gas, with the concomitant greenhouse gas emissions of 2.3 to 16 tons carbon dioxide emitted per ton of ammonia produced.

In addition to its use as a chemical or as a component in the production of fertilizer, ammonia can also be used as a hydrogen carrier through simple decomposition of ammonia to hydrogen and nitrogen when needed. Ammonia can also be used directly as a fuel for internal combustion engines.

Existing technology for ammonia production (Haber-Bosch process based on iron catalyst) is over 100 years old. This process requires large amounts of natural gas (North America and Europe), coal (mainly China), or Naphtha (e.g., India) as a fossil energy source and to supply hydrogen. The process is also technologically complex as the ammonia formation must be conducted under very high pressures (up to 290 atm) and temperatures (around 400-600° C.). What is needed is a way to produce ammonia and hydrocarbons in a cost effective manner that is less damaging to the environment, and preferably utilizing renewable or green energy.

SUMMARY OF THE INVENTION

According to one embodiment of the present invention there is provided a composition having the general formula $AEMD_{n-\delta}O_{m-\varepsilon}$, wherein A is a cation, E is an optional anion or anionic group or electrons providing electroneutrality of the bulk composition, M is a transition metal, D is a non-metal selected from the group consisting of carbon and nitrogen, O is oxygen. The two non-metals, D and O have variable concentrations, $n-\delta$ and $m-\varepsilon$, respectively, where n and m are $>0$, $n>\delta\geq 0$, and $m>\varepsilon\geq 0$. The composition is variable between a filled state, in which $n-\delta$ is maximized and $m-\delta$ is minimized, and an empty state, in which $n-\delta$ is minimized and $m-\varepsilon$ is maximized.

According to another embodiment of the present invention there is provided a solid reactant capable of supplying a non-metal element during a chemical reaction occurring substantially at atmospheric pressure and resulting in the formation of a product comprising the non-metal element. The reactant comprises first and second non-metals, a cation, and a transition metal. In particular embodiments, the first non-metal element is selected from the group consisting of carbon and nitrogen, and the second non-metal is oxygen. In particular embodiments, the transition metal is selected from the group consisting of Group 4 to 9 transition metals and the lanthanides. In particular embodiments, the cation selected from the group consisting of alkali and alkaline earth metal cations. The transition metal and at least one of the two non-metals, and optionally the cation, form a crystal lattice wherein at least a portion of the first non-metal may be removed from the lattice upon reaction of the reactant with a compound comprising the second non-metal. The reaction results in the formation of the product compound, and possibly the addition of at least a portion of the second non-metal contained in the compound to the lattice.

According to another embodiment of the present invention there is provided a method of making a solid reactant comprising first and second non-metals, a transition metal, and a metal cation, the solid reactant providing a source of the first non-metal for a chemical reaction resulting in the formation of a product comprising the first non-metal. The method comprises the steps of: (a) providing a reactant precursor comprising the transition metal; (b) reacting this reactant precursor with a source of the first non-metal at a total pressure of less than 10 atm and a temperature of between about 500° C. to about 2000° C. to form the solid reactant; and (c) introducing a metal cation, and optionally an anion, anionic group or electrons, into the reactant precursor of step (a) or the solid metal compound of step (b) compound to form the solid reactant composition that is electronically neutral at the bulk-scale, the metal cation being introduced in the form of a metal or a cation in the presence of an anion or anionic group.

According to still another embodiment of the present invention there is provided a method of producing a compound comprising a first non-metal and hydrogen. The method comprising the steps of: (a) providing a solid reactant material comprising the first non-metal and a second non-metal, a transition metal, a cation, and an optional anion or anionic group or electrons; and (b) reacting the solid reactant material with steam at a pressure of less than 10 atm and a temperature of at least 200° C. to produce the compound and a spent reactant material. The spent reactant material has a lower ratio of the first non-metal to the second non-metal than the solid reactant material.

DETAILED DESCRIPTION OF THE PREFERRED EMBODIMENT

Certain materials of the present invention were developed based on a new rationale for non-catalytic ammonia synthesis related to metal nitride iconicity. The usefulness of these compositions of matter is in general to balance the opposing requirements in certain chemical reaction networks by adding a cation to an existing inorganic reactant, where the presence of the cation promotes a portion of the reaction network that would otherwise be an insurmountable obstacle to realizing the particular desired reaction network and thereby production of the desired product under economically and technically attractive conditions. Of particular interest are chemical reaction networks attempting the chemical reduction and hydrogenation of a non-metal or of non-metal compounds.

In certain embodiments, materials according to the present invention allow for production of hydrocarbons, such as methane or acetylene from flue gas or synthesis gas (carbon dioxide or carbon monoxide), air, and sunlight, and ammonia or hydrazine from air, water and sunlight in an economically attractive process having significant advantages over the current state of the art hydrocarbon or ammonia syntheses. The material balances efficient breaking of the $N_2$ triple bond (for ammonia production) or CO bond (for hydrocarbon synthesis) followed by hydrogenation of the reduced carbon or nitrogen to hydrocarbons or $NH_3$, respectively. Hydrogen is supplied in form of water, not from natural gas (as is the current practice). Hydrogenation of the non-metal is promoted by deliberately added cations present in the composition. The cation supports the liberation of hydrogenated non-metal from the bulk of the solid reactant. The cation may be electrically balanced at the bulk-scale by specific anions, present in the form of an oxide, hydroxide or carbonate, for example, or the cation may be balanced by electrons, presenting itself thereby in the form of a suitable secondary metal. In particular, steam hydrolysis of manganese nitride promoted with sodium cations, in the form of sodium hydroxide, was found to yield readily and quickly by a factor of about 100, more $NH_3$ as compared to ammonia yields in the absence of the sodium cation promoter. As distinguished from conventional catalysts, the cation promoted transition metal reactants may contain non-metal defects substituted with oxygen. Generally, the reactants achieve hydrogenation of non-metals directly with water as the hydrogen source, as opposed to hydrogen abstracted from fossil fuels.

Materials according to the present invention are reactants that can be employed for reduction and hydrogenation of stable non-metal compounds. Existing technology achieves this in a single, high-temperature and high-pressure step by the use of catalysts. The process described herein uses two separate steps but advantageously, the reaction can be conducted at near ambient pressure (that is the reactants are at chemical equilibrium with the non-metal with a chemical activity equivalent to ambient pressure).

Because the synthesis can be undertaken at ambient pressure, and under moderately high temperatures, it is possible to use solar heat to drive the reaction resulting in the formation of, for example, ammonia or hydrocarbons. Therefore, the reactant material can be seen as a storage and transport option for intermittent solar energy. The energy stored in solar thermochemical ammonia can be used in agriculture for fertilizers, but also as a hydrogen carrier through simple decomposition of ammonia to hydrogen and nitrogen when needed, or as a fuel where ammonia is directly used in internal combustion engines. Similarly, acetylene, or other hydrocarbons may also be used for hydrogen storage, or directly as a fuel.

In certain embodiments of the present invention, the reactant is a stoichiometric or non-stoichiometric material comprised of a transition metal (M), a suitable cation (A), and first and second non-metals (D) and (O). In particular embodiments, the material has the general formula $AEMD_{n-\delta}O_{m-\varepsilon}$, wherein, E is an optional anion or anionic group or electrons providing electroneutrality of the bulk reactant. The two non-metals, D and O have variable concentrations, $n-\delta$ and $m-\varepsilon$, respectively. In certain embodiment, where n and m are $>0$, $n>\delta\geq0$, and $m>\varepsilon\geq0$. The values of n and m are dependent upon the particular transition metal (M) present in the composition. As explained in greater detail below, the composition is variable between a filled state, in which $n-\delta$ is maximized and $m-\varepsilon$ is minimized, and an empty state, in which $n-\delta$ is minimized and $m-\varepsilon$ is maximized. Relative to the concentration of the transition metal, n, in certain embodiments, can be in the range of approximately 0.25 to 0.5, if M is selected from Group 7 to 9 transition metals, or 0.5 to 1, if M is selected from Group 4 to 6 transition metals. Relative to the concentration of the transition metal, m varies largely upon the choice of M and is in most cases in the range of approximately 1 to 3. In certain embodiments, n and m are related by the equation $n+m=c$, where c is constant and within the range of about 0.1 to 30 relative to the molar concentration of M. Both, $\delta$ and $\varepsilon$ are variable (varying upon the materials composition and the reaction condition). Generally, $\delta$ and $\varepsilon$ are not correlated by the non-metal product that the reactant may produce when employed in a reaction cycle. In particular embodiments, $\delta$ and $\varepsilon$ are relatively large, approaching the value of n and m, and are correlated through the number of non-metal-hydrogen bonds of the non-metal product that the reactant may produce. For instance, for ammonia synthesis with water as hydrogen source a ratio of $\varepsilon/\delta=1.5$ is desirable to avoid by-production of diatomic hydrogen.

The cation can be either a dopant at the atomic scale, forming a part of the crystal lattice of the reactant, or part of a physical mixture of nano- or micro-sized particles. In certain embodiments, the cation is an alkali or alkaline earth metal cation, such as potassium, sodium, or calcium and may be present in said composition at a ratio of between about $10^{-6}$ to $5\times10^0$ of mol A to mol M, between about $10^{-3}$ to about $2.5\times10^0$ of mol A to mol M, or between about $10^{-2}$ to about $10^0$ of mol A to mol M. Also, the cation can be electronically balanced by electrons or anions (E) such as for example oxide, superoxide, hydroxyl, or carbonate anions.

In certain embodiments, the first non-metal (D) may be nitrogen or carbon, and the second non-metal may be oxygen. The nitrogen or carbon may comprise a solute in the reactant or may be present as part of the crystal lattice, yielding in any case a stable nitrogen- or carbon-containing compound at ambient pressure (that is, in thermochemical equilibrium with 1 atm nitrogen gas or the equivalent concentration of carbon). In certain embodiments, the molar ratio of the first non-metal to the second non-metal in the reactant composition is between about $10^{-5}$ to about $10^5$, between about $10^{-3}$ to about $10^3$, or between about $10^{-2}$ to about $10^2$.

In certain embodiments, the transition metal (M) is selected from the group consisting of Group 4 to 9 transition metals and the lanthanides. In particular embodiments, the transition metal is selected from the group consisting of cerium and Group 6 to 7 transition metals (e.g., chromium, molybdenum, tungsten, and manganese).

In certain embodiments of the present invention, the material comprises a solid reactant capable of supplying a non-metal element during a chemical reaction occurring substantially at atmospheric pressure and resulting in the formation of a product comprising the non-metal element. The transition metal and at least one of two non-metals, and optionally the cation, form a crystal lattice wherein at least a portion of the first non-metal (D) may be removed upon reaction of the reactant with a compound comprising the second non-metal (O). The reaction results in formation of the product compound, at least a portion of the second non-metal contained in the compound being added to the product. Thus, in one sense, these materials are reactants and storage devices for non-metals and energy. In their, per definition, "empty state" ($AEMD_{n-\delta}O_m$) these compositions contain a minimum concentration of the non-metal D ($n-\delta>0$) and a maximum concentration of the second non-metal O ($m>0$ and $\varepsilon=0$). In their, per definition, "filled state" ($AEMD_nO_{m-\varepsilon}$) the compositions contain a maximum concentration of the non-metal D ($n>0$ and $\delta=0$) and a minimum concentration of the second non-metal ($m-\varepsilon>0$).

The following equations are exemplary of "filling" of the reactant with nitrogen (D=N) or a gaseous source of carbon (D=C), by complete transformation of the "empty state" into the "filled state".

Emptying of the "filled" reactant may be utilized for hydrogenation of nitrogen or carbon in the solid to ammonia ($NH_3$) or hydrocarbons ($C_aH_b$) respectively, for instance using water as hydrogen source. The following equations are exemplary of this "emptying" reaction, describing the complete transformation of the "filled state" into the "empty state".

In certain embodiments of the present invention, the solid reactant can be synthesized via a number of schemes that are explained in greater detail below. However, generally, the reactant is synthesized by first providing the transition metal, either in pure form or in form of a transition metal compound. This reactant precursor is reacted with a source of the first non-metal (either contained in the reactant precursor or supplied externally) to form a solid containing the transition metal and at least the first non-metal. The reactant is completely synthesized after introduction of the cation, either alone (electronically balanced, i.e., in form of a metal) or in combination with the optional anion or anionic group. The cation may be introduced either into the reactant precursor or into the solid containing after reacting reactant precursor with the source of the first non-metal.

The solid comprising at least the first non-metal and transition metal can be prepared in several ways. In one embodiment, this involves reducing a precursor compound comprising the transition metal and the second non-metal in the presence of said first non-metal. In particular embodiments, the precursor compound comprises a transition metal oxide or hydroxide. In one exemplary embodiment, a salt-like precursors of the transition metal (e.g., molybdenum (IV) oxide or manganese oxide-hydroxide, i.e., MnO(OH), powder) is reduced in presence of nitrogen (such as molecular nitrogen) or carbon (such as gas mixtures containing carbon monoxide, methane or other hydrocarbons) and possibly hydrogen gas as reducing agent. In another embodiment, preparation of the compound comprising the first non-metal and transition metal comprises the vapor decomposition of a transition metal amine or a transition metal hydroxyl compound. For example, this step may comprise vapor decomposition of transition metal amine (e.g., tetraamminedichlorochromium(III) chloride) or carboxyl (e.g., tungsten hexacarbonyl) compounds, possibly in presence of hydrogen gas as reducing agent. In yet another embodiment, the compound comprising the first non-metal and transitional metal comprises reacting a metallic powder comprising the transition metal with a source of the first non-metal. For example, the metallic powders may be reacted with a source of nitrogen (such as molecular nitrogen) or carbon (such as gas mixtures containing carbon monoxide, or hydrocarbons, especially $C_1$-$C_4$ hydrocarbon compounds, and particularly, methane).

The reactant precursor material is reacted with one or more gaseous compounds comprising the first non-metal to form a reactant product that is "filled" with the first non-metal. In certain embodiments, the gaseous compound may comprise molecular nitrogen gas, when the first non-metal is nitrogen, and carbon monoxide or a hydrocarbon compound (e.g., $C_1$-$C_6$ hydrocarbon compounds), when the first non-metal is carbon. In particular embodiments, this reaction occurs at a pressure of less than 10 atm, less than 5 atm, less than 2 atm, or about 1 atm. In certain embodiments, this reaction occurs at a temperature of between about 500° C. to about 2000° C., between about 600° C. to about 1500° C., or between about 700° C. to about 1240° C. The heat introduced so as to elevate the temperature of the reactants at this stage may be provided via various means known to those of skill in the art, including the electrical or fossil fuel burning ovens. However, in one particularly preferred embodiment, the heat is supplied via solar radiation, such as through the use of a solar furnace. Details regarding the construction of an exemplary solar furnace are disclosed in Michalsky et al., Chromium as reactant for solar thermochemical synthesis of ammonia from steam, nitrogen, and biomass at atmospheric pressure, *Solar Energy* 85 (2011) 2642-2654, the entirety of which is incorporated by reference herein. In Michalsky et al., solar radiation was concentrated in a reactor using a Fresnel lens mounted in a mobile scaffold.

The introduction of the cation may then be achieved in one of various ways. In one embodiment, the crystalline lattice of the compound comprising the first non-metal and transition metal may be doped with the metal cation. For example, the doping may occur by diffusion of potassium into the lattice of solid tantalum carbide particles heated in liquid potassium. In another embodiment, the precursor material is formed by physically mixing the compound comprising the first non-metal and transition metal with a material comprising the metal cation and the anion or anionic group. For example, this can be accomplished by milling solid manganese nitride powder with solid sodium hydroxide powder using a ball mill or pestle and mortar.

The above-described methods for forming the reactant material may automatically lead to the introduction of the second non-metal, e.g., oxygen, into the reactant. For example the second non-metal may be present as an impurity, such as traces of water present in the solid or gaseous feedstock chemicals, or as an inherent and desirable constituent of the feedstock, such as the lattice oxygen of sodium hydroxide. Also, as described further below, it is a major application of these reactant materials to facilitate the conversion of water into hydrogen-containing chemicals such as ammonia, methane or ethane. This too will lead to the incorporation of the second non-metal, namely oxygen, into the reactant material when brought into contact with water. Independent of the source of second non-metal as constituent of the reactant, it is understood that various concentrations of the second non-metal can be present in the reactant materials described herein. This is in contrast to common catalysts employed for the catalytic formation of ammonia or hydrocarbons.

In this context it should be noted that the presence of the first non-metal (especially, nitrogen or carbon) yields reactant materials that are thermodynamically stable (i.e., will not form other energetically more stable compounds at a certain stable temperature, total pressure near 1 atm, and stable chemical activities of all present chemical species). Thereby, compositions based on materials that are unstable near ambient pressure such as certain iron nitrides (catalysts for the catalytic ammonia formation at the conditions of the Haber-Bosch process) or silver carbide, for instance, are excluded here.

The solid reactant materials produced according to certain embodiments of the present invention may be provided as powders, made into pellets, or loaded onto a support substrate, such as a metal oxide. It is further noted that the reactant material may be synthesized in situ on the support substrate. For example a transition metal oxide support may be the precursor compound from which the reactant is generated.

As discussed above, the reactant materials may be used to generate compounds comprising the first non-metal and hydrogen under generally milder conditions than could be accomplished using conventional catalytic reactions. In certain embodiments, these methods generally comprise providing a solid reactant material, such as any of those described herein, and reacting the solid reactant material with water, preferably in the form of steam, to produce the product compound and a spent reactant material. The spent reactant material generally has a lower ratio of the first non-metal to the second non-metal than the initial solid reactant material due to usage of the first non-metal in formation of the product compound. In addition, additional quantities of the second non-metal, namely oxygen supplied by the water, may become incorporated into the crystal lattice of the reactant material.

When the first non-metal is nitrogen, the products produced via reaction of the solid reactant material generally comprise ammonia and/or hydrazine. When the first non-metal is carbon, the products produced generally comprise hydrocarbon compounds, particularly $C_1$-$C_4$ hydrocarbon compounds, and especially methane, ethane, ethylene, and acetylene.

In certain embodiments according to the present invention, this "emptying" of the reactant material occurs at pressure conditions similar to the "filling" reaction, particularly at a pressure of less than 10 atm, less than 5 atm, less than 2 atm, or about 1 atm. The temperature at which the "emptying" reaction occurs is also relatively mild when compared to previous catalytic reaction schemes for producing the product compound. In certain embodiments, this reaction occurs at a temperature of at least 200° C., between about 300° C. to about 600° C., or between about 400° C. to about 500° C. As with the "filling" reaction described above, the heat required for the "emptying" reaction may be supplied via any means known to those of skill in the art; however, the use of solar radiation is especially preferred.

Figure 2:
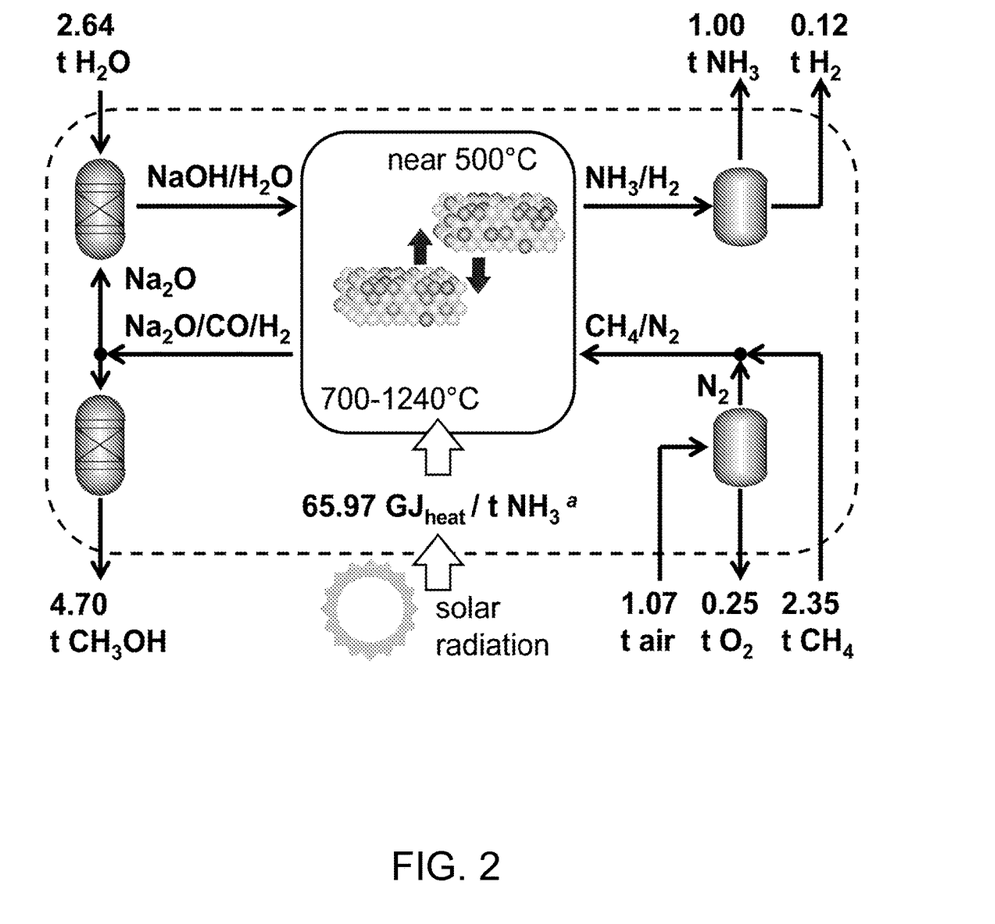
FIG. 2 is a schematic diagram depicting the filling and emptying of a sodium ion-promoted manganese nitride reactant using concentrated solar radiation.

Once emptied, the spent reactant material may be "refilled" or regenerated much in the same way as the reactant precursor material is initially filled with the first non-metal, such as through reaction with molecular nitrogen or a carbon source. This scheme is also depicted in FIG. 2, with respect to ammonia production.

EXAMPLES

The following examples set forth various exemplary reactants and reaction schemes according to the present invention. It is to be understood, however, that these examples are provided by way of illustration and nothing therein should be taken as a limitation upon the overall scope of the invention.

Example 1

Synthesis of Sodium Ion-Promoted Manganese Nitride

Manganese nitride (64-67 wt % ε-$Mn_4N$, 25-36 wt % ζ-$Mn_6N_{2.58}$, 46±19 μm average particle diameter, 270±3 $m^2$ $kg^{-1}$ specific BET surface area) was synthesized by heating 2.0-3.0 g Mn metal for 2 h at 700° C. in a flow of 1.8±0.1 $L_{(STP)}$ $N_2$ $min^{-1}$.

The heating rate, rH, was about rH=At+B, where t is the heating time in min, A=−6.91° C. $min^{-2}$, and B=77.4° C. $min^{-1}$). The cooling rate was in the range of −13.5 to −2.73° C. $s^{-1}$ within the first 60 s, −3.85 to 0.767° C. $s^{-1}$ at 60 to 180 s and >−0.767° C. $s^{-1}$ at >180 s.

Figure 1:
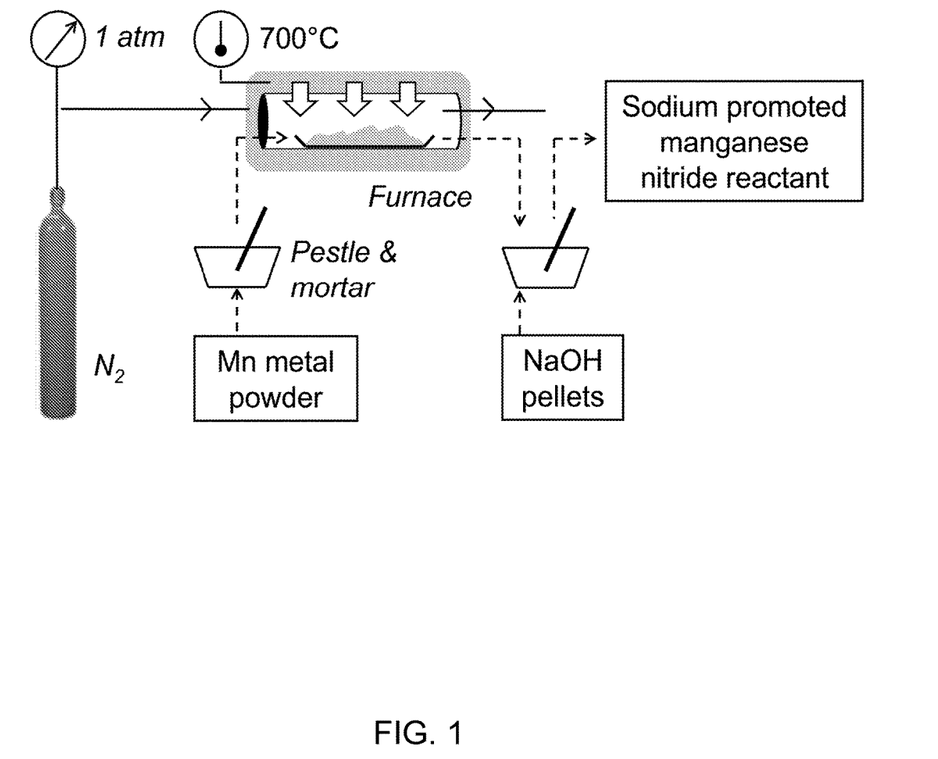
FIG. 1 is a schematic diagram of an exemplary process for synthesizing a sodium ion-promoted manganese nitride reactant according to one embodiment of the present invention from manganese metal powder, sodium hydroxide pellets and nitrogen gas.

The material was promoted with $Na^+$ via milling 0.47±0.06 g nitride (2.3±0.2 mmol lattice nitrogen) with 1.02±0.01 g NaOH (99.6%, certified ACS pellets) using pestle and mortar. The synthesis scheme is schematically depicted in FIG. 1. As a comparative example, the material was promoted with 0.483±0.001 g $Ca(OH)_2$/CaO (97.3% pure, 75 wt % CaO, 25 wt % $Ca(OH)_2$.

Use of Sodium Ion-Promoted Manganese Nitride

FIG. 2 illustrates an exemplary scheme for both filling and emptying of the reactant. The top portion of FIG. 2 depicts "emptying" of the sodium ion-promoted manganese nitride compound using water and heat. The bottom portion depicts "filling" of the reactant using atmospheric nitrogen and methane (that is activated concurrently for by-production of a mixture of CO and hydrogen, e.g., syngas, the precursor for the synthesis of various liquid fuels) and heat. In the schematic, the heat is supplied via solar radiation; however, any economically feasible heat source may be employed.

To assess the formation of $NH_3$ by reacting alkali or alkaline earth metal promoted manganese nitride with steam, the sodium and calcium promoted materials were distributed evenly in a quartz boat. The boat was heated in the tube furnace at 48±18° C. min$^{-1}$ from 100-500° C. Temperatures were held for 60 min and steam was supplied at 0.8±0.1 mL $H_2O$ min$^{-1}$. The formation of $NH_3$ was followed using a liquid absorbent (25±5 mL 10 mM HCl, chilled with ice-cold $H_2O$).

Powder X-ray diffraction (XRD) and energy-dispersive X-ray spectroscopy (EDS) were employed for quantitative solid phase identification. All solids were analyzed gravimetrically. The specific BET surface area of manganese nitride was analyzed. $NH_3$ absorbed by the liquid absorbent was quantified with an $NH_3$ Ion Selective Electrode and a pH/ISE Controller, combined with the liquid level in the absorption vessel (error about ±5 mL). Liquid samples were analyzed in triplicate to estimate the concentration of dissolved $NH_3$ with zeroing for the signal from pure water. $NH_3$ concentrations for experiments employing Na$^+$ doped nitride reactant were verified using a sodium nitroferricyanide-based colorimetric assay at the Kansas State University Soil Testing Laboratory, Manhattan, Kans. The outlet of the absorption vessel was equipped with an $NH_3$ gas detection tube.

In general, the addition of $CaO/Ca(OH)_2$ decreased the yield of $NH_3$, e.g., from 1.0±0.2 mol % $NH_3$ after 5 min in absence of the oxide/hydroxide to 0.23±0.05 mol % $NH_3$ after 5 min in presence of the oxide/hydroxide. See, FIG. 3 (error propagation within a 95% confidence (error bars) yields in average±21.78%). Dashed lines represent shrinking-core models limited by solid-state diffusion. A diffusion-limited kinetic model describes the data well. Furthermore, the reaction yielded $Mn_3O_4$ and MnO at an atomic $Mn^{3+}/Mn^{2+}$ ratio of 1.31 or 0.14 in absence or presence of $CaO/Ca(OH)_2$ respectively, indicating that the calcium compounds significantly decreased the oxidation of Mn. See, FIG. 4 (a, the atomic ratio of metallic constituents in the reactive material, error propagation within a 95% confidence (error bars) yields in average±18.32%). This may be due to additional mass transport limitations of the steam to the nitride due to $CaO/Ca(OH)_2$ and/or may indicate that $Ca^{2+}$ is not a suitable dopant for manganese based reactants. However, it should be understood that these results are not necessarily indicative that $Ca^{2+}$ would not be a suitable dopant for other transition metal-based reactants.

Figure 3:
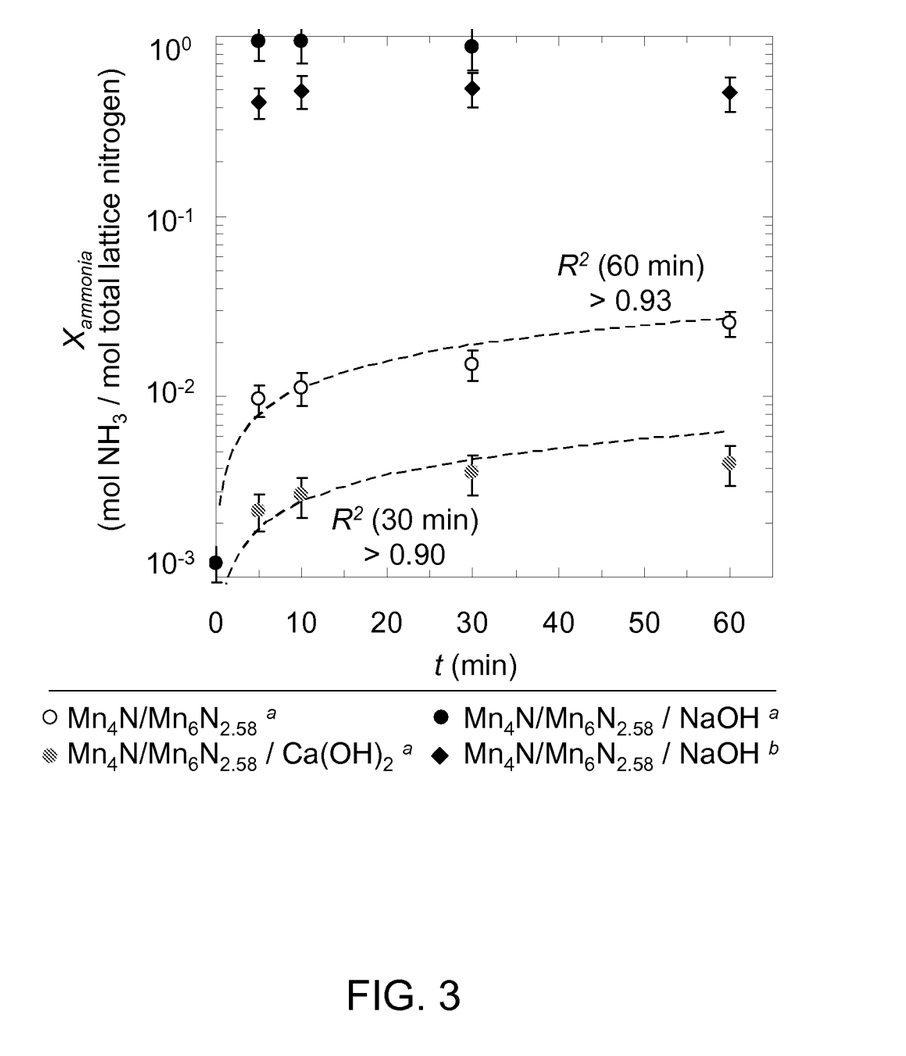
FIG. 3 is a graph of the yield of $NH_3$ reacting manganese nitride in presence or absence of $Ca^{2+}$ or $Na^+$ dopants with steam (500° C. and near 1 bar)
Figure 4:
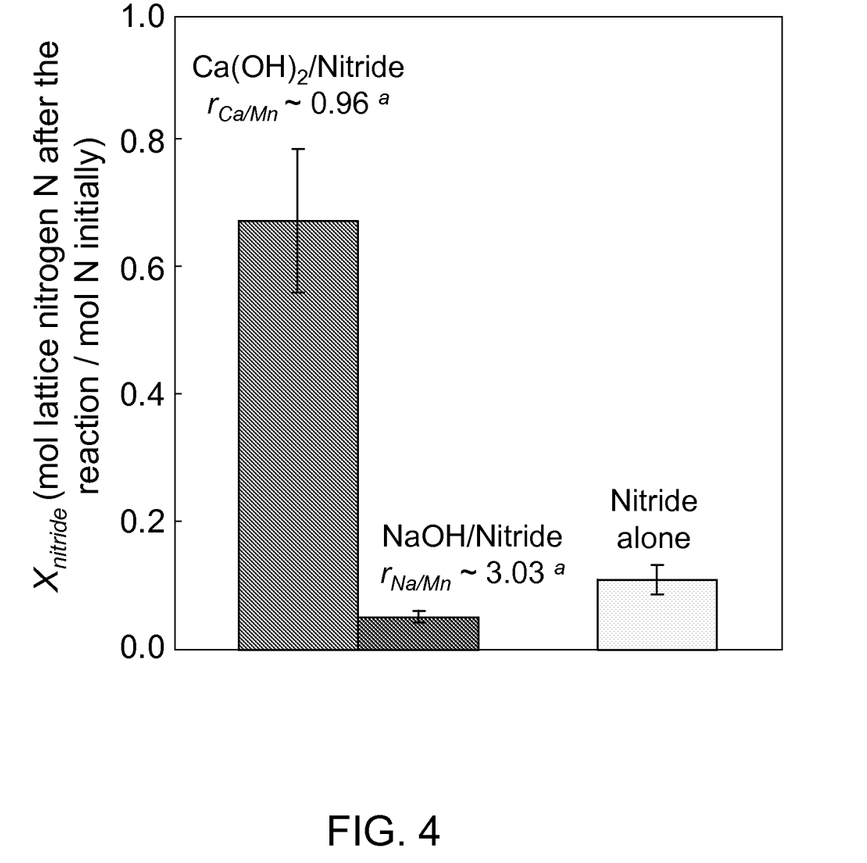
FIG. 4 is a chart illustrating the fraction of nitrogen recovered in the reactant after corrosion of $Mn_4N/Mn_6N_{2.58}$.

The addition of NaOH increased the formation of $NH_3$ yielding 43-94 mol % $NH_3$ after 5 min (FIG. 3). The relative broad range of this estimate is due to conducting the experiment in duplicate and analyzing with two different techniques for $NH_3$. The mechanism limiting the formation kinetics is uncertain due to the employed analytical method that is inadequate to capture the quick $NH_3$ formation kinetics in presence of NaOH with high accuracy. The formation of $Na_2MnSiO_4$ ($SiO_2$ presumably from the corroded quartz boat) as the major products in the solid state, along with manganese compounds retaining minor traces of nitrogen (FIG. 4), illustrates that the sodium cation retained its oxidation state (Na$^+$ as NaOH initially vs. Na$^+$ as $Na_2O$ after the reaction). Therefore, after reloading the reactant with nitrogen (from $N_2$), the sodium promoter is expected to increase the activity of the hydroxyl ion when reacting the material anew with water. Furthermore, the thereby established basic reaction environment presumably supports conversion of adsorbed $NH_4^+$ to gaseous $NH_3$. This may promote the kinetics of the ammonia formation due to promoted desorption yielding new reactive sites.

Therefore, it was discovered that promotion of manganese nitride with sodium cations in form of sodium hydroxide increased the yield of ammonia via hydrolysis at 500° C. from 2.4-2.8 mol % (in absence of Na$^+$) to 43-94 mol % (in presence of Na$^+$). Reaction kinetics were also improved by about two orders of magnitude from 9.7±0.9×10$^{-6}$ mol $NH_3$ mol$^{-1}$ Mn s$^{-1}$ at 500° C. (in absence of Na$^+$) to 4-9×10$^{-4}$ mol $NH_3$ mol$^{-1}$ Mn s$^{-1}$ (in presence of Na$^+$).

Na$^+$ promoted manganese nitride may be supported on porous manganese oxide that is providing a high specific surface area of the supported reactive material. This may be achieved by partly converting a porous manganese oxide starting material into manganese nitride (growing on the surface of the oxide) followed by doping with sodium (see above). If utilizing a support material, matching the composition of the support with the reactant may ensure long-term stability of the reactant due to decreased differences in the thermal expansion coefficients and avoided solid-state reactions between the reactant and the support.

The reactant may be placed into a packed-bed reactor that allows for (i) supply of gases (steam, atmospheric nitrogen and a reducing agent such as methane) and (ii) reception of concentrated solar energy (via a solar receiver such as small quartz window).

The product (ammonia) may be formed in a semi-continuous way, that is, by controlling the reactor temperature and gas compositions:

First, at ambient pressure and at relative low temperatures (near 300-500° C.) hydrolysis of the reactive material with steam will yield ammonia. Ammonia can be separated from the outlet steam/ammonia mixture via condensation or adsorption. This reaction will cause oxidation of the reactant with formation of sodium manganate on the surface of the reactant.

Second, introduction of a methane/nitrogen gas mixture at ambient pressure into the reaction chamber that is heated via the incident solar energy to about 1000-1250° C. restores the original reactant composition. The gas mixture exiting the reaction chamber will be composed of carbon monoxide, hydrogen, unreacted methane, unreacted nitrogen and fractions of volatile sodium compounds such as $Na_2O$. The sodium compounds can be recycled via condensation and rerouting into the reactor. Dependent on the stoichiometric composition of the remaining gas, the $CO/H_2/CH_4/N_2$ mixture may be utilized, directly or after adjusting the concentrations of CO and $H_2$, for subsequent synthesis of chemicals and fuels. Neither hydrogen nor carbon has been consumed from the methane feedstock. This enables the by-production of chemicals such methane ($CH_3OH$) or liquid hydrocarbons via the Fischer-Tropsch process.

Third, ammonia and the byproducts will be produced semi-continuously via cyclic repetition of step one and two.

In light of California starting to implement an actual carbon offset trade market, in the best-case scenario these materials will allow for synthesis of ammonia or hydrocarbons without any fossil carbon dioxide emission (besides indirect $CO_2$ generation for auxiliary electric consumption). This may be realized if the reducing agent can be avoided or originates from a renewable resource such as water or biomass. The worst case scenario, that is use of fossil methane as reducing gas, would lead to conversion of a fossil resource to methanol (or similar) which can be utilized in a way that does not lead to emission of $CO_2$ (flue gas of Haber-Bosch plant that cannot be concentrated and recycled in an economically attractive fashion vs. recyclable concentrated $CO_2$, for instance from a methanol fuel cell). A recent process analysis of molybdenum-based reactive ammonia formation yielded total $CO_2$ generation in the range of 0.62-1.08 tons $CO_2$ per ton $NH_3$; that is a reduction of up to 50-96% relative to the industrial ammonia synthesis with a natural gas or coal feedstock.

Example 2

Hydrocarbons from Alkali/Alkaline Earth Metal-Promoted Transition Metal Reactants with Carbon Contained in the Solid Reactant Given the chemical similarities between metal nitrides and metal carbides, cation promoted transition metal reactants containing carbon in the solid state can reveal a capability for hydrogenation of the secondary non-metal (carbon) that is comparable to the functionality of the cation promoted transition metal reactants containing nitrogen in the solid state.

This assessment is based on comparable bonding properties (metal-nitrogen bond vs. metal-carbon bond) in the solid state, which is determined by ionic, covalent and metallic "contributions" to the cohesive energy of the solid. In nitrides as well as in carbides, this leads to formation of complex band structures mainly due to the interactions of the metallic d-orbitals and the non-metallic p-orbitals. These bonding characteristics can be regarded as an intermediate state between the metallic bonding found in pure or alloyed metals on one hand and the strongly localized bonding, best-described via molecular orbital theory, found in salts on the other hand. In fact, these "intermediate bonding characteristics" together with the generally stronger and localized bonding between the metal and oxygen are central to the functionality of the reactive compositions according to the present invention. In the "filled state" the reactants give stability and reactivity to the non-metal (nitrogen or carbon) that is stored in the material due to partly-covalent and partly-ionic bonding with the metal. On the other hand, the stronger bonding between oxygen and the metal provides the reactive material with the ability to form carbon or nitrogen vacancies that can be filled with oxygen.

Figure 5:
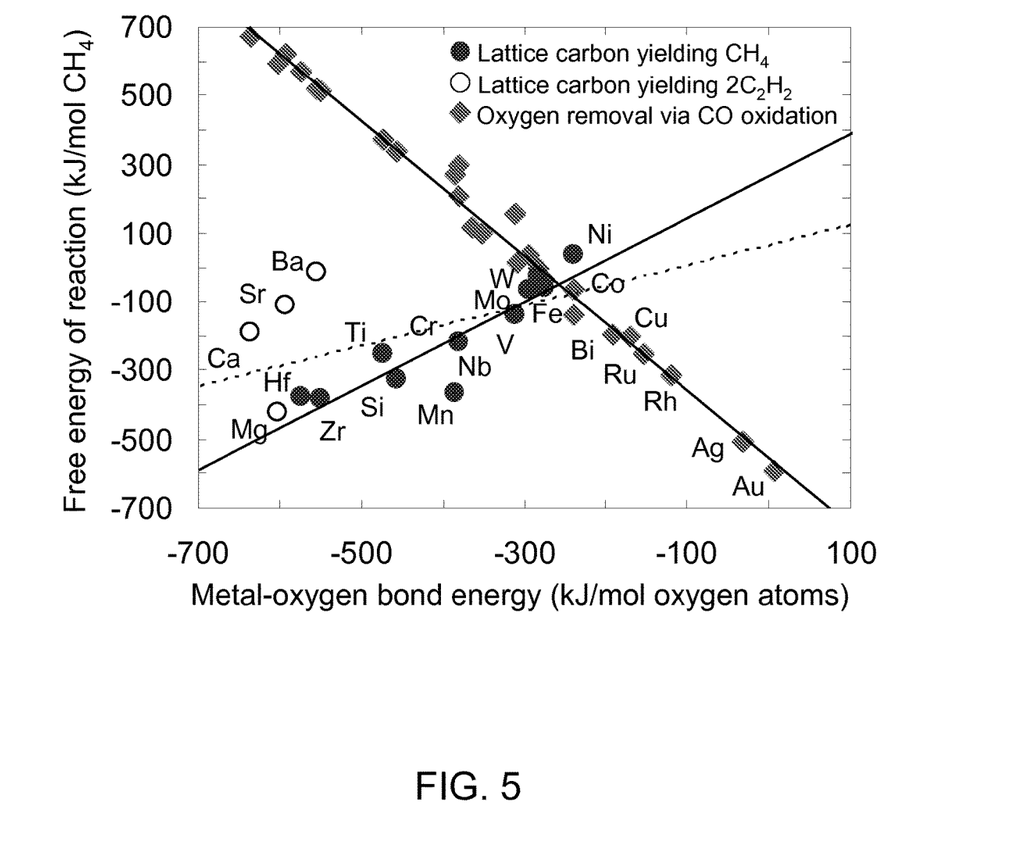
FIG. 5 is a plot illustrating screening for the transition metal component of the lattice carbon-containing reactants for thermochemical hydrocarbon production.

FIG. 5 is a plot of oxygen removal from stable metal oxides at 727° C. (reactant recycling) or lattice carbon hydrogenation from stable metal carbides at 327° C. at ambient pressure versus the bonding energy of metal and oxygen atoms (metallic constituents indicated only). This thermochemical analysis shows that the choice of the transition metal component (the metals found on top of the volcano-shaped curve) of these compositions containing lattice carbon is equivalent to the transition metal choice for the compositions containing lattice nitrogen.

The analysis plots the free energy of the capability for oxygen removal (oxide reduction with carbon monoxide oxidation to carbon dioxide as example) or hydrogenation of the lattice carbon (with water yielding one mol methane or 2 mol acetylene if the major metal constituent, M, is an alkaline earth metal, a case included here for completeness, see further below) vs. the enthalpy of the metal-oxygen bond as a common descriptor. Based on free energy analysis, methane is the most likely hydrogenation product. However, other hydrocarbons are expected to form as well. In the case of the well-known alkaline earth metal carbides, stoichiometry and the ionic bonding in the these solids leads to formation of acetylene (here taken as 2 mol $C_2H_2$ to match the formation of 4 C—H bonds for the $CH_4$ formation). The net-reaction accomplished in this example is the conversion of CO and $H_2O$ to $CH_4$ and $CO_2$, and in some cases $C_2H_2$ and/or $H_2$. This illustrates the ability of the above-described reactants to be used for formation of hydrocarbons at ambient pressure. If the required temperatures are supplied via solar radiation the reactants accomplish storage of solar energy in the reaction cycle product resulting in a sustainable hydrocarbon fuel.

Since the top of the "pseudo-volcano" (FIG. 5) represents negative free energy values for either one of the two computed reactions, the optimum metal components (M) of the above-described compositions are metals such as Mo, W, Fe, or Co. Since metal reduction can be achieved as well with hydrogen in addition or alternative to carbon monoxide (see, *Solar Energy* 85 (2011) 2642-2654), Cr, Nb, Mn, or Ti can be suitable transition metal components also. Therefore, this thermochemical analysis for materials with lattice carbon confirms the choice of the transition metal component of the above described compositions from group 4 to 9. FIG. 5 indicates also that certain other metals (for example Mg, Ca, Sr, and Ba or Ag and Au) have an only limited activity for either "filling" or "emptying" reactions and are unable to achieve the desired trade-off in their redox capacities.

This conclusion can be understood in analogy to the Sabatier principle employed in catalysis. The Sabatier principle states that the interactions between a catalyst and the substrate are a trade-off between the adsorption energy of reactants and products on the catalyst surface. Optimally, adsorption energies are strong enough to absorb reactants on the catalyst surface (to facilitate their conversion into products) but weak enough to allow for desorption of products (to avoid blocking the surface for continued conversion). For reactive materials such as the compositions described herein, this principle appears to translate into "the ideal metal reactant forms a bond with a non-metal (nitrogen, carbon, or oxygen) in the bulk material that is strong enough to capture and store the non-metal in the solid state but weak enough to allow for its removal". Such removal may be achieved either via formation of stronger bonds to oxygen or via supply of energy in form of heat, solar heat for example. The latter enables possible storage of solar energy. The same principle applies: if the metal-oxygen bond is too weak (e.g., in the case of Au- or Ag-based reactants in the above analysis) no solar energy can be stored, but also, if the metal-oxygen bond is too strong (e.g., in the case of Mg- or Ca-based reactants) storage of solar energy and removal of oxygen would require temperatures that would, in many cases, destroy the reactant (evaporation) or that would be very difficult to realize in an industrial furnace.

Furthermore, transition metals that form non-stoichiometric oxides that liberate readily a fraction of their lattice oxygen at elevated temperatures are suitable for use as the major metal component of the described materials. This includes the lanthanides in general and cerium in particular.

Given the analogy of these carbon-containing materials to the nitrogen-containing materials, utility of a cation dopant can be inferred from the experimentation on nitrides discussed above.

Carbon-containing materials formed by the transition metals discussed above, such as Mo or Mn, are expected to form hydrocarbons. Such exothermic hydrogenation of the lattice carbon of these materials will thermodynamically favor low temperatures that likely impose kinetic limits. Also, the superior hardness, high melting points and in particular the minor net-ionicity and an essentially non-locally distributed electronic charge of the interstitial carbides (including groups 4-6, i.e., including Cr, Mo, W, utilized as refractory tools for machining and as refractory materials) supports the expected diminished functionality of these materials for hydrocarbon generation due to kinetic limitations. The "distorted" (not simple octahedral) crystal structures of the intermediate metal carbides (including group 7-9, i.e., including Mn, Fe, Co) and the increased ionic contributions in their d-p bands will only to some extend alleviate these limitations, partly at costs of a diminished capability to store the carbon in the solid.

Therefore, the addition of a suitable cation from groups 1-2 is expected to donate to the reactive material the ability of liberating its carbon, under suitable reaction conditions (analogous to those conditions described for "emptying" the reactive materials compositions, described above), without impairing its ability to store carbon in its "filled state". The cation is expected to promote corrosion (breaking metal-carbon bonds and forming metal-oxygen bonds) if desired, hydrogenate the lattice carbon (for instance with protons obtained from splitting water into protons and hydroxyl ions), or promote desorption of the formed carbohydrates (perhaps partly due to affecting the dipole interaction on the materials surface). Lewis acid ($NH_4^+$)-base ($NH_3$) interactions during desorption of ammonia that is presumably affected by the cation dopant of the nitrogen-containing reactants play likely a less important role for the carbon-containing reactants (methane and other hydrocarbons are very weak acids).

Formation of hydrocarbons via hydrolysis of the cation-promoted carbon-containing reactants is a major application of these materials. A packed-bed reactor heated at ambient pressure via solar concentration is one such practical implementation.

The possible reaction products will be determined by the reaction conditions as well as by the bonding of the reactive materials. For the above covered materials compositions, methane is the most likely hydrocarbon product at near ambient reaction conditions. However, dependent on the electronic configuration of the carbon in the solid and the electronic and geometrical surface bonding properties, formation of higher hydrocarbons, including $C_2$ hydrocarbons, such as acetylene, ethylene and ethane are possible products, besides methane.

As a simplified example, exothermic hydrolysis of the lattice carbon of molybdenum semicarbide yielding molybdenum dioxide favors low temperatures. At a relatively moderate 327° C., the reaction is thermodynamically feasible (exergonic) if methane (−65.7 kJ/mol lattice carbon) or ethane (−30.3 kJ/mol lattice carbon) are formed, along with hydrogen due to excess water. Carbon-carbon bonds within the reactive material such as presumably for Mn-based reactants may increase the yield of higher hydrocarbons. A suitable cation promoter is expected to increase the speed with which these products can be formed.

We claim:

1. A method of producing a compound comprising a non-metal D and hydrogen comprising the steps of:
   (a) providing a solid reactant material having the general formula $AEMD_{n-\delta}O_{m-\epsilon}$ wherein A is a cation, E is an optional anion or anionic group or electrons providing electroneutrality of the solid reactant material, M is a transition metal, non-metal D is carbon, and O is oxygen, where n and m are >0, n>$\delta$≥0, and m>$\epsilon$≥0, wherein the solid reactant material is provided in a filled state, in which n−$\delta$ is maximized and m−$\epsilon$ is minimized, said transition metal, said non-metal D, said oxygen, and, optionally, said cation forming a crystal lattice;
   (b) reacting said solid reactant material with steam at a pressure of less than 10 atm and a temperature of at least 200° C. to remove at least a portion of said non-metal D from said crystal lattice and produce said compound and a spent reactant material in an empty state, in which n−$\delta$ is minimized and m−$\epsilon$ is maximized, said spent reactant material having a lower ratio of said non-metal D to said oxygen than said solid reactant material; and
   (c) regenerating said solid reactant material by reacting said spent reactant material with a gaseous compound comprising said non-metal D,
   wherein during step (b), O atoms are added to said crystal lattice while said portion of said non-metal D is removed from said crystal lattice,
   wherein during step (c) atoms of said non-metal D are added to said crystal lattice while atoms of O are removed from said crystal lattice.

2. The method according to claim 1, wherein said solid reactant material is provided in the form of a powder.

3. The method according to claim 1, wherein said solid reactant material is provided in pelletized form.

4. The method according to claim 1, wherein said solid reactant material is loaded onto a support.

5. The method according to claim 1, wherein said step (b) comprises reacting said solid reactant with steam at a pressure of less than 2 atm and a temperature of between about 300° C. to about 600° C.

6. The method according to claim 1, wherein said compound produced in step (b) is a hydrocarbon compound.

7. The method according to claim 6, wherein said hydrocarbon compound is a $C_1$-$C_4$ hydrocarbon compound.

8. The method according to claim 1, wherein heat introduced during step (b) is supplied via solar radiation.

9. The method according to claim 1, wherein said gaseous compound in step (c) is CO and/or $CO_2$.

10. The method according to claim 9, wherein said CO and/or $CO_2$ is supplied diluted with $H_2$.

11. The method according to claim 1, wherein heat is introduced during step (c), said heat being supplied via solar radiation.

12. The method according to claim 1, wherein A is an alkali or alkaline earth metal cation and is present in said solid reactant material at a ratio of between about $10^{-6}$ to $5\times10^0$ of mol A per mol M.

13. The method according to claim 1, wherein E is selected from the group consisting of oxide, superoxide, hydroxyl, and carbonate anions.

14. The method according to claim 1, wherein M is selected from the group consisting of Group 4 to 9 transition metals and the lanthanides.

15. The method according to claim 1, wherein n is between about 0.25 to about 1.

16. The method according to claim 1, wherein m is between about 1 to about 3.

17. The method according to claim 1, wherein n and m are related by the equation n+m=c, wherein c is constant and within the range of about 0.1 to 30.

* * * * *